United States Patent [19]

Pflugbeil

[11] Patent Number: 5,573,010
[45] Date of Patent: Nov. 12, 1996

[54] PROBE FOR MEDICAL PROCEDURES IN CAVITIES OF THE BODY

[75] Inventor: Peter Pflugbeil, Munich, Germany

[73] Assignee: Eckart Frimberger, Munich, Germany

[21] Appl. No.: 240,715

[22] PCT Filed: Nov. 12, 1992

[86] PCT No.: PCT/EP92/02606

§ 371 Date: Aug. 1, 1994

§ 102(e) Date: Aug. 1, 1994

[87] PCT Pub. No.: WO93/09835

PCT Pub. Date: May 27, 1993

[30] Foreign Application Priority Data

Nov. 18, 1991 [DE] Germany ............... 41 37 950.0

[51] Int. Cl.$^6$ ....................................... A61B 5/00
[52] U.S. Cl. ................................................ 128/772
[58] Field of Search ........................... 128/657, 658, 128/772; 604/95, 164, 280–283

[56] References Cited

U.S. PATENT DOCUMENTS

| | | | |
|---|---|---|---|
| 4,757,827 | 7/1988 | Buchbinder et al. | 128/657 |
| 4,811,743 | 3/1989 | Stevens | 128/657 |
| 4,886,067 | 12/1989 | Palermo | 128/657 |
| 4,940,062 | 7/1990 | Hampton et al. | 128/657 |
| 5,001,825 | 3/1991 | Halpern | 128/772 |
| 5,133,364 | 7/1992 | Palermo et al. | 128/657 |

*Primary Examiner*—Max Hindenburg
*Attorney, Agent, or Firm*—Scully, Scott, Murphy & Presser

[57] ABSTRACT

In a probe (1) for medical procedures in cavities of the body, consisting of an elastically flexible sheath (2), which over at least one longitudinal section is formed by sheath elements (11) lying one after another in the longitudinal direction, and a core (3), there is provided in the rearward region of the probe (1) between the sheath (2) and the core (3) such a fixing (5a, 5b) that by bending (B) of the probe (1) in the rearward region thereof, projecting out of the body cavity, a relative displacement between the sheath (2) and the core (3) takes place.

12 Claims, 7 Drawing Sheets

PROBE FOR MEDICAL PROCEDURES IN CAVITIES OF THE BODY

Probes of this kind are used in various fields of medicine, namely for therapeutic or diagnostic purposes in body cavities of the body to be treated, in particular for the introduction into the digestive or excretory tract.

Such a probe has a basic function, namely a relative displacement between the sheath and the core for the purpose of carrying out a specific function or manipulation in the body cavity.

With a probe having a sclerosation cannula a forwardly directed thrusting movement of the core is utilized for the purpose of injection. To this end, the core is manually advanced inside the sheath.

With a so-called controllable guiding probe with a deflectable probe tip, which is suitable in particular for seeking and introduction into bodily cavities progressing transversely, a driving device effective between the sheath and core is provided at the rearward end of the probe, by means of which driving device a pulling force and displacement directed to the rear can be effected manually upon the core, to bring about the deflection at the probe tip. For the purpose of retracting the probe tip, the core is manually pushed forwards with the aid of the driving device.

A configuration comparable in principle with the one described above is also present in a so-called biopsy probe, wherein the biopsy forceps are opened by means of the driving device through manual forward displacement of the core, and the biopsy forceps are closed by manually pulling the core backwards.

With so-called stiffening probes an axial compression of the sheath, consisting of elements arranged one after the other, is achieved by pulling action on the core, to the rear, producible manually by a tensioning device arranged at the rearward end of the probe. Here, the core exercises a tensioning force on the sheath, in the forward region of the sheath, whilst the sheath is supported in the rearward region by the separate tensioning device.

In many cases the probe, in its condition as inserted into the body cavity, is used as guiding element or guide rail for numerous medical instruments, such as in angiography catheters or dilatation instruments, which are advanced into the desired area of the body on the probe.

To carry out the relevant procedure, the probe is firstly inserted into the desired cavity structure of the body, e.g. inserted into the bile duct from the duodenum by means of an endoscope which is perorally introduced. The appropriate instrument is then advanced along the probe into the desired target area. In the case of the bile duct the instruments are often hollow probes (drains) which, in the case of tumorous constriction of the bile duct (malign stenosis), are pushed through the constriction and left in place. They bridge the stenosis thereby to ensure the drainage of the gall bladder.

There are two main requirements of such a probe, namely on the one hand a high degree of flexibility, for low risk introduction and placing of the probe, and on the other hand a certain rigidity, especially for guiding purposes, e.g. stable guiding when carrying out bougienage, placing drains, etc. By means of purposive stiffening of the probe the difficulty of a loop forming can be overcome, e.g. when traversing the stomach.

Such a known probe, as described in the EP-A-0 131 847, ideally fulfils the above-described conflicting requirements. In a relaxed state the probe makes possible an atraumatic placing thereof, and by tensioning the desired rigidity of the probe can be set. The probe consists of an elastic flexible sheath, in which a core is longitudinally displaceably guided, the length of the core being considerably greater than the length of the sheath. The core has a ball-like stop part on its forward end and a disc-like stop on its rearward end, whereby both parts are rigidly attached to the core. The extra length of the core is required to enable a tensioning device to be applied between the sheath and the core, and to be able to pull the core in its longitudinal direction, in order to draw the stop part of the core, in its forward end region, up against the forward end of the sheath and thereby stiffen the probe. For this purpose the tensioning device is applied between the rearward end of the sheath and the rearward disc-like stop, whereafter with the moveable tensioning element of the tensioning device a pulling force may be applied to the core, which leads to stiffening of the probe.

The tensioning device has spindle drive for the axial movement of its tensioning element.

A probe of the latter kind is also described in the US-A-4 215 703. With this known probe the tensioning device is formed by two sleeves, coaxially arranged on the sheath one after the other in the region in which, at the rearward end of the probe, the core projects rearwardly beyond the sheath, the rearmost sleeve being rotatable relative to the forwardmost sleeve. Thereby the two ends of the sleeves facing one another are formed as inclined or tilted planes, which are lie on the other in parallel in the initial disposition of the tensioning device. Through relative rotation of the two sleeves to one another, the inclined planes cause an extension thereof, whereby a pulling force is exerted on the core, attached to the rearmost sleeve, which causes the stiffening of the probe.

However, the known probes are disadvantageous with regard to their constructional outlay and the effort required for their operational or technical handling. The former is determined by the presence of the driving or tensioning device, which represents considerable constructional outlay, and also results in a bulky construction for the probe, which makes the handling of the probe more difficult. The latter consists in that in particular the tensioning device requires considerable manual force and operational effort—even when it does not additionally have to be mounted on the probe—whereby the person carrying out the procedure has to carry out an activity which hinders the treatment itself or the positioning of the probe in the specific insertion position for each case. Thus, the measures to be carried out for the treatment in each case are affected and the handling and manipulation are made more difficult.

The object of the invention is to reduce the constructional outlay and handling effort for a probe of the kind described in the introduction.

This object is achieved by the features of claim 1. Further advantageous developments of the invention are described in the subclaims.

For the probe according to the invention, no additional driving or tensioning device is required. At least no such driving or tensioning device is required which is supported at the rearward end of the sheath and which pulls the core rearwardly out of the sheath. The relative displacement can be caused by bending the sheath once or several times. Herewith the desired simpler form of construction is achieved, since no additional driving or tensioning device is required, and also a simpler handling is achieved, since the probe, i.e. the sheath and core, simply need to be bent, which can be easily effected without requiring heightened attention from the person carrying out the treatment. It is even possible to effect the bending of the probe with the fingers of one and the same operating hand, so that the other hand of the person carrying out the treatment can be used for other treatment activities, so that one-handed operation is provided.

The object of the present invention is, amongst other things, based on two primary features, namely that the core is fixed in its rearward region to the sheath, in the rearward region of the sheath, and that a longitudinal displacement between sheath and core is achieved by a common bending. By bending the core from its straight disposition to a curved disposition, a shortening of the core as compared to the sheath is achieved, so that the front end of the core is drawn into the sheath. Consequently the core can exert a tensioning or pulling force. On the other hand, if the probe is bent from its curved disposition into its straight disposition, the relative displacement thereby occurring results in a forward movement of the forward end of the core relative to the sheath, thereby enabling the core to exert a pushing or thrusting force.

The above-mentioned fixing between core and sheath need be effective only in one direction, and can therefore be formed by displacement movement limiting stops. In the case in which the core exerts a pulling force directed rearwardly, the entry movement of the core with respect to the sheath is to be limited in the rearward region of the probe. In the case in which the core exerts a pushing force directed forwards, the retraction movement of the core with respect to the sheath is to be limited. Of course, it is also possible to make the fixing between core and sheath in the rearward region of the probe immovable, e.g. by clamping, welding, soldering or gluing.

In the case in which the pulling force of the core is utilized to exert an axial compression on the sheath, a second fixing between sheath and core is necessary in the forward region of the probe. This fixing also need only be effective in one direction, as merely an entry of the core, in the forward end region of the probe, with respect to the sheath, needs to be limited, for which purpose a pair of longitudinal displacement limiting elements can serve. However, it is also possible in this case to immovably fix the core and sheath in the forward region of the probe, e.g. by clamping, welding, soldering or gluing. The above-mentioned compression upon bending of the probe in the rearward region thereof results in the desired stiffening of the probe.

The solution according to the invention thus rests upon an idea which is completely different from the known probe. With the known probe, the sheath is immovably fixed by the driving device and the core is pulled rearwardly from its rearward end. With the solution according to this invention, however, a relative displacement between the core and the sheath occurs through the bending of the probe, with which functions and manipulations can be effected, e.g. the exertion of a pushing force or pulling force, or the compression of the sheath.

As a slight longitudinal displacement between sheath and core occurs during insertion of the probe into curved body cavities, a tolerance for some displacement should be predetermined, in particular if a fixing of sheath and core is also provided in the forward region of the probe.

The length of the displacement tolerance is determined by the number and size of the twists and turns in the bodily cavity in which intervention is to occur as well as by the length and/or degree of bending of the probe. If required, the probe can be wrapped several times around the finger or the hand of the person carrying out the treatment. It is significant that, with the compression of the sheath, the displacement tolerance is taken up by the bending of the probe, whereafter an axial tension between the sheath and the core is effective on account of the bending, leading to the desired stiffening.

In the case in which a relative displacement is to be achieved merely by the bending of the probe in the rearward region thereof, there should be taken into account a displacement tolerance with regard to the intended goal of the desired movement.

By bending back the probe, which, on account of the elasticity of the sheath, occurs automatically after lateral bending of the probe, when the probe is let go, the movement or action arising according to the invention is traced in reverse.

With the invention the desired movement of the core or the above-described displacement tolerance is limited by the fixing between the sheath and core in the rearward region of the probe. Such a form of fixing on the probe is not present in the known probes.

A suitable form of sheath is one which is preferably formed by an elastic wire or spring wire, wound in a coil-like manner, or by an equivalent band. It is thereby possible within the scope of the invention that several or all windings have a spacing from one another, whereby the total of these spacings can correspond to the displacement tolerance. With this configuration a smoother rigidity characteristic at the beginning of stiffening can be obtained on account of the spring resilience of the individual windings in the longitudinal direction. It is possible to form a wound sheath in such a way that the windings directly contact one another. In this configuration, the displacement tolerance is provided by a spacing between the rearward limiting element pair.

Within the scope of the invention it is also possible for the sheath to be formed by members arranged one after the other, as is represented in FIGS. 15 and 16 of the above-mentioned EP-A-0 131 847 and described in the corresponding text. Reference is made to the full extent of this description.

According to the configuration in accordance with the invention the stiffening probe can be formed symmetrically with regard to the longitudinal center thereof, so that there is no difference in terms of configuration between the forward and rearward ends thereof. The probe according to this invention can therefore be used bilaterally.

In the subclaims features are contained which contribute to problem solving and lead to a simple, stable and economically producible construction, further simplify handling and further improve functionality.

In the following the invention and further advantages which can be achieved thereby will be described in more detail with reference to preferred embodiments and the drawings, in which.

The probe according to FIGS. 1 to 10 is a so-called stiffening probe, which can be inserted without stiffening into the bodily cavity of a body to be treated, and can then be stiffened. The probe 1 consists of a sheath 2, closed in the circumferential direction of the probe, and a core 3 displaceable in the longitudinal direction thereof with clearance for motion, whereby displacement limiting element pairs 4a, 4b, 5a, 5b are effective between the sheath 2 and the core 3, are arranged with axial spacing, in the respective end regions of the probe 1, and prevent a displacement of the sheath 2 on the core 3 which exceeds a predetermined amount.

The core 3 consists in each case of a flexible wire or band or a flexible braid. As material, metal is suitable, in particular steel or plastics. The core is somewhat elastic, so that after bending out of its normally straight extension it readily springs back into its original form. The limiting element pairs 4a, 4b, 5a, 5b, corresponding with one another, are each formed by a thickened core head 6 or 7 attached to the associated end of the core 3 and the associated end 8, 9 of the sheath 2. The core heads 6, 7 are preferably metal heads, which are fastened permanently to the core 3, e.g. by soldering, welding, adhering, or pressing. The core heads 6,7 are preferably ball-like and have a cross-sectional size which prevents slipping through the sheath 2.

The sheath 2 consists of an elastic band or wire, wound in the manner of a helix, of plastic or metal, in particular spring wire, whereby windings 11 one behind the other in longitudinal direction are provided.

The free internal cross-section of the sheath 2 is so dimensioned that the wire or band of core 3 has therein radial play for movement.

Figure 1:
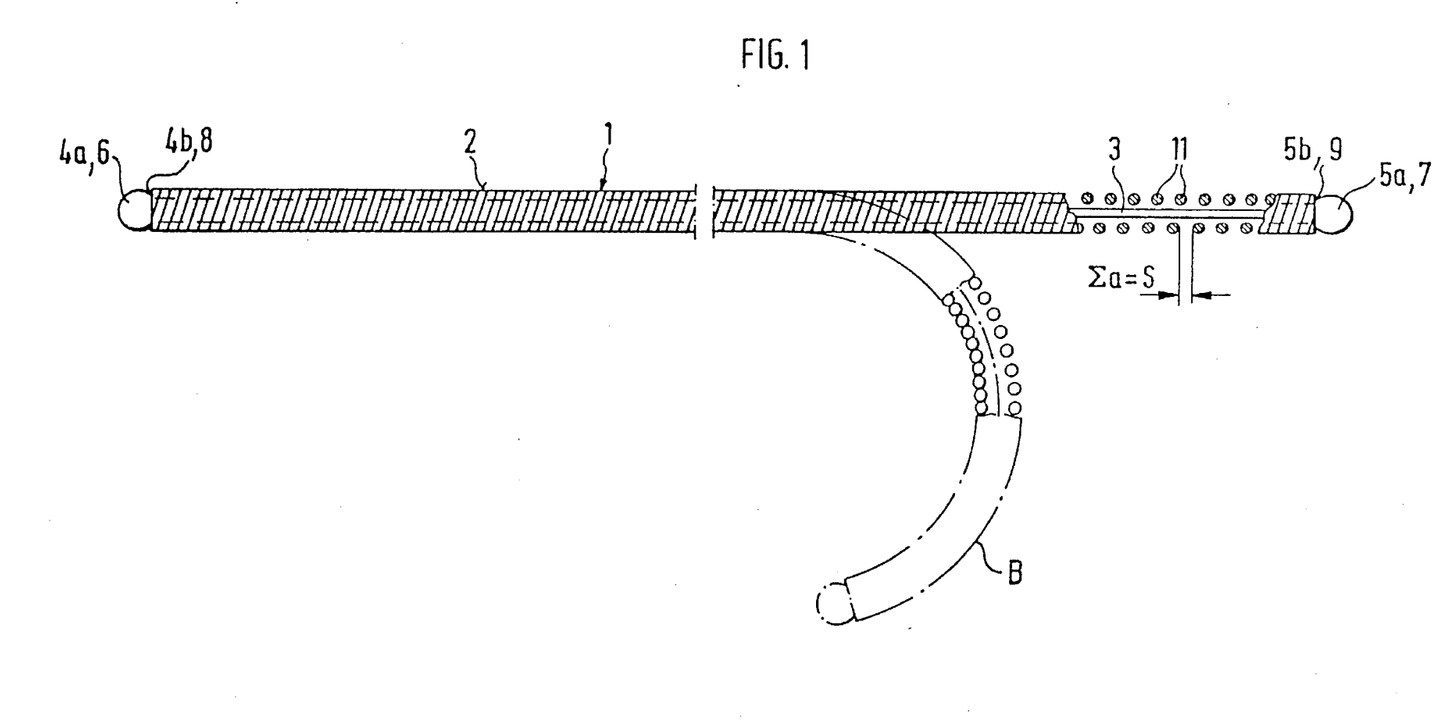
FIG. 1 shows a probe formed according to the invention in a non-stiffened, straight, neutral disposition and, schematically indicated, in a bent, stiffened disposition.

In the configuration according to FIG. 1 the individual windings 11 exhibit a spacing a from each other, which can approximately correspond to the winding diameter or is preferably slightly smaller. This spacing a can either be purposely wound or it is also possible to provide the spacings a by stretching the sheath 2 beyond its limit of elasticity. The core 3 is of such a length that the core heads 6,7 thereof bear, in the neutral, i.e. non-bent condition of sheath 2, against the ends 8,9 of sheath 2. The core heads can also be at a small spacing from the ends 8,9 and can also bear against the ends 8,9 under slight tension. If a probe according to FIG. 1 is bent, the windings 11 on the inside of the bend approach each other and come into mutual abutment, whereby at this point a stiffening of probe 1 already occurs on account of the axial tension between core heads 6, 7 and the sheath 2. With further bending B, the tension and stiffening is increased. On the outer side of the bend B the windings 11 remain spaced apart from each other.

The total of the spacings a between the windings 11 yields an amount which is to be termed displacement tolerance S and is neutralized on the inside of the bend B by bending of the probe 1, as can be perceived from the schematic representation in FIG. 1.

The strength or rigidity of the stiffening is determined by the degree of bending B and/or the length of the bend. Tight bending and/or a long bend leads to a strong stiffening. Thereby, on account of the axial spacings of the windings 11 from each other, there is provided a smooth rigidity characteristic. By unbending of the bend B the stiffening is removed.

Figure 2:
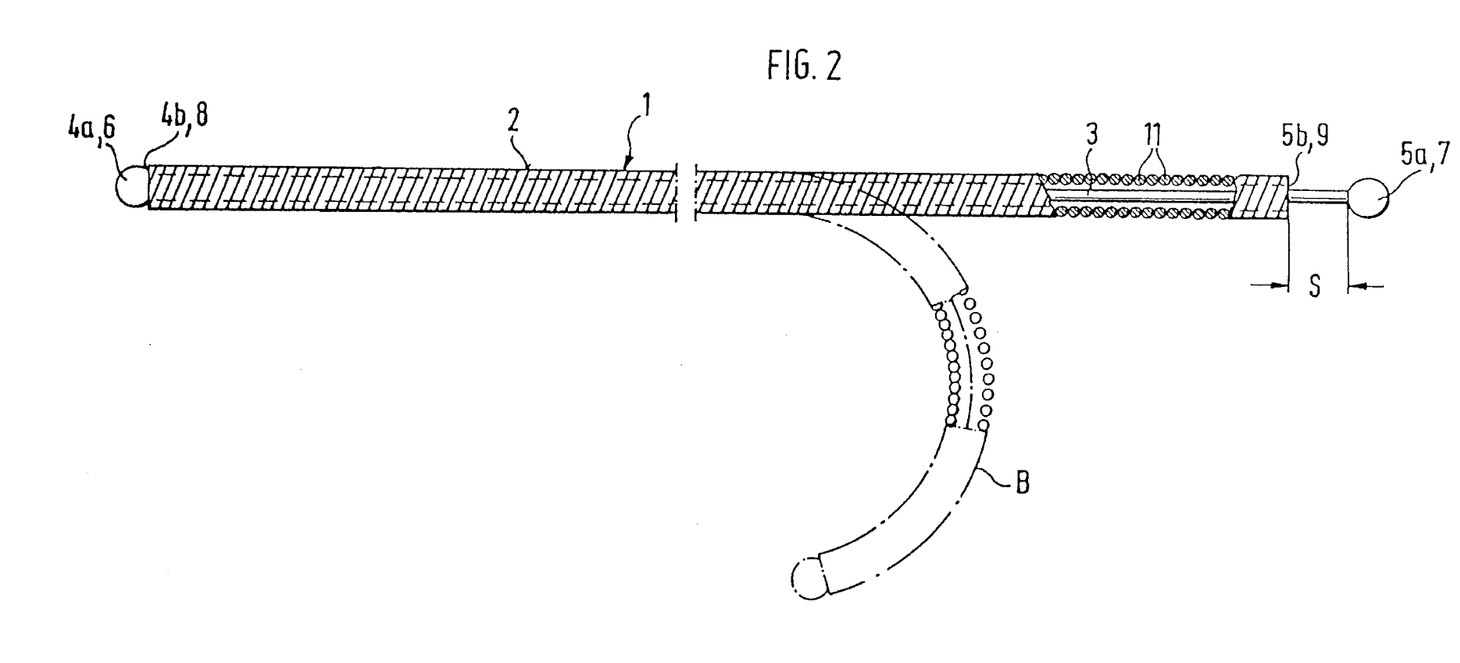
FIG. 2 shows a probe formed according to the invention in a non-stiffened, straight, neutral disposition and, schematically indicated, in a bent, stiffened disposition as a second embodiment.

The configuration according to FIG. 2 differs from that described above in that the windings 11 have no axial spacing a from one another, but lie against each other. Thereby, in the straight neutral position according to FIG. 2 the length of core 3 is such that a core head, in this case the rear core head 7, has a spacing from the corresponding end 9 of the sheath which corresponds to the displacement tolerance S. As the core 3 is freely displaceable in sheath 2, both core heads 6,7 can of course exhibit a spacing from the corresponding ends 8,9, whereby the total of these two spacings corresponds with the displacement tolerance S.

When, in the configuration of FIG. 2, the probe is bent, the displacement tolerance S is taken up in a similar way as in the above-described embodiment, whereafter axial tensioning between the sheath and the core, and stiffening, is caused by this or further bending B. On the inner side of the bend B, the windings 11 remain in mutual contact whilst the windings are spaced apart on the outer side of the bend B, as illustrated in the region of the bend B in FIG. 2. The taking up of the displacement tolerance S can be recognized in that the core head 7 contacts the facing end of the sheath 2. In this disposition certain stiffening is already provided. By the exercise of further tensioning, by bending, the stiffening is increased.

In both the above-described configurations the probe 1 is, with regard to its ends, similarly formed: i.e. the forward and the rearward end of the probe 1 are similar and the probe can therefore be introduced into the body to be treated with either one of the ends.

Figure 3:
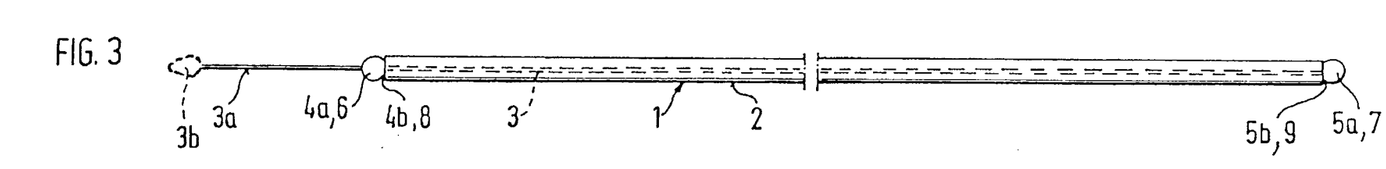
FIGS. 3 to 7 show probes according to the invention in modified configurations.
Figure 4:
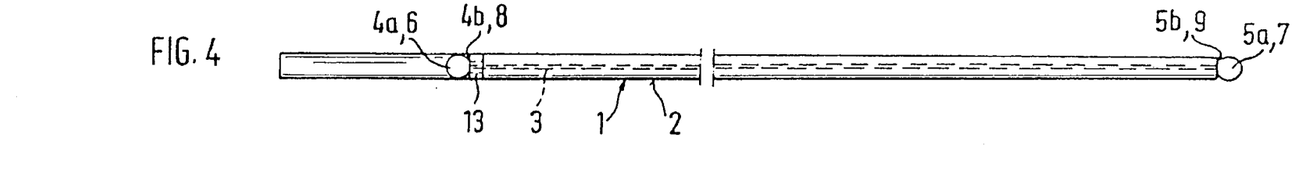
Figure 5:
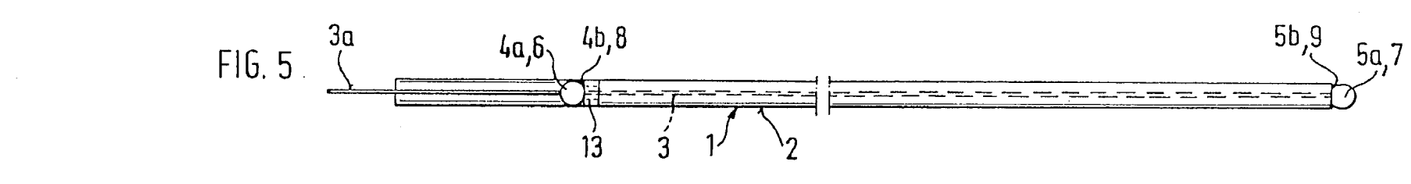

As FIGS. 3 to 5 show, the displacement limitation element pairs 4a, 4b, 5a, 5b need not be arranged on the ends of probe 1. According to FIG. 3, one probe section 3a extends forwardly from the forward core head 6, having on the free end thereof an in particular round head-shaped thickening 3b, as is schematically indicated in FIG. 3. The thickening 3b preferably exhibits the axial sectional form of a cone, the rounded tip thereof pointing forwards, whereby the cone is also either rounded, conically chamfered, or bevelled on its rear side. The thickening 3b is welded, glued, or preferably soldered. According to FIG. 4 the sheath 2 is, at the forward or rearward end, extended beyond the associated core head 6, whereby the sheath-side displacement limitation element part is formed by an inside shoulder 13 within the sheath 2, which can be formed by a ring attached therein.

FIG. 5 shows a combination of the configurations according to FIGS. 3 and 4, namely a forward core head 6 sunk in the sheath 2 lying against an inside shoulder 13, from which core head an initial core section 3a likewise extends forwardly.

Figures 6, 8:
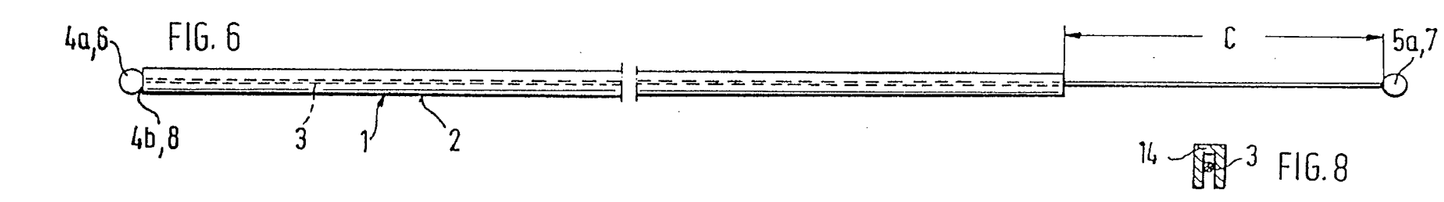
FIG. 8 shows the section VIII—VIII in FIG. 7.
Figure 7:
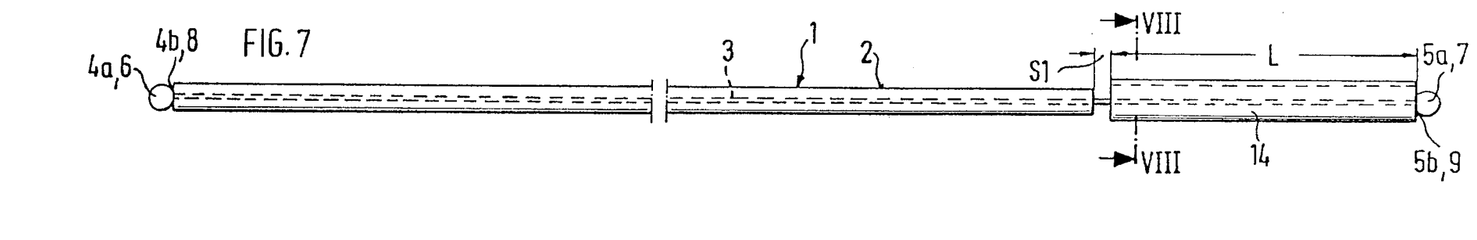
Figure 9:
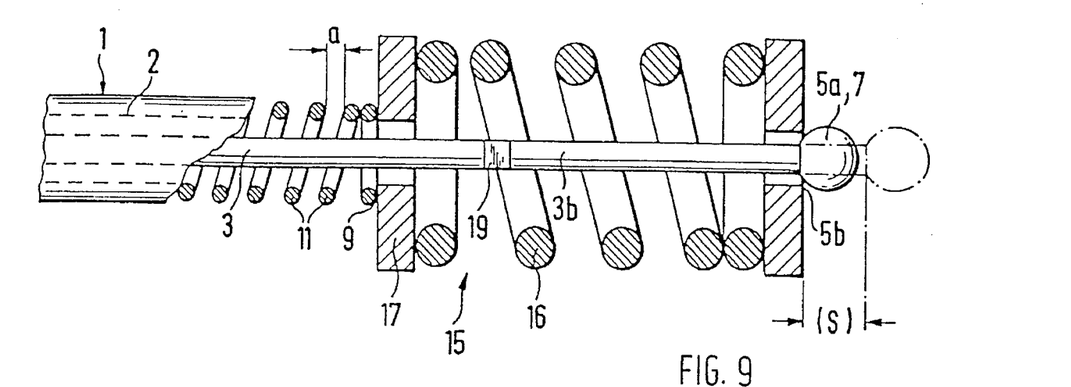
FIG. 9 shows a probe according to the invention with a measuring device for the longitudinal displacement of the core thereof or for the tension force present.

With the configuration of probe 1 according to the FIGS. 6 to 8 the core heads 6, 7 have a spacing from one another which is significantly greater than the length of the sheath 2, so that at the rearward end a spacing C between the core head 7 and the sheath 2 occurs which is significantly greater than the displacement tolerance S in the above-described configurations.

Such a probe 1 has associated therewith a spacer 14, which bridges the spacing C. The spacer 14 is laterally mounted onto the core 3, preferably clamped on. A U-shaped cross-sectional form is suitable for the spacer 14, whereby the core 3 is taken up between the limbs of the U-form, or is manually releasibly wedged between the limbs.

Preferably the probe 1 has associated therewith several spacers 14 of different lengths and definite length gradations. Hereby it is possible to utilize one and the same probe 1 for various procedures on the body, e.g. in more or less curved or loop-form body cavities, whereby, after inserting the probe into the body to be treated, a spacer 14 appropriate in terms of its length to the resulting spacing C can be chosen and mounted. By means of the length of the spacer 14, a desired displacement tolerance S1 can, if appropriate, be set, and thereby also the degree of the bending B can be set.

All above-described configurations are suitable for a probe 1 on which the windings 11 are spaced at spacing a (FIG. 1), as well as for a probe on which the windings 11 lie against each other (FIG. 2). In the former case it is advantageous to choose a spacer 14 with a length L corresponding to the spacing C. In the latter case a spacer can be chosen, the length of which likewise corresponds with spacing C or is somewhat shorter, the displacement tolerance S1 resulting from the difference between spacing C and length L.

When utilizing stiffening probe 1 according to the invention there is a danger of tearing the band or wire of the core by overtensioning the probe 1, possibly when wrapped several times, e.g. around the hand of the user, whereby the connection of probe 1 with the front core head is broken and the core head 6 cannot be extracted from the body together with probe 1. In order to avoid such an overtensioning or overloading of the core 3, according to FIGS. 9 and 10 the probe 1 has associated therewith a tension/pulling force indicating device 15, which measures the exerted pulling force and visually indicates the force via an indicator element. This indicator device 15 is mounted coaxially of the probe 1 at the rearward end thereof, i.e. the device projects from the probe 1 to the rear, and consists of a compression spring 16 which is rigidly held on the rearward end of the sheath 2, e.g. by means of an intermediate ring 17, e.g. by welding, soldering or gluing. The core 3 extends as a preferably one-piece extension 3b through the compression spring 16, whereby the rearward core head 7 is attached to the rearward end of this extension 3b. With a configuration of the probe 1 according to FIG. 1 with a spacing a between the windings 11, the rearward core head 7 can be arranged on the rearward end of the compression spring 16 or on an end ring 18 attached thereon, as has been described similarly for the first embodiment. With such a configuration, the required displacement tolerance S is determined by spacings a. With a configuration of the probe 1 with windings resting against each other according to FIG. 2, the displacement tolerance S is to be provided between the rearward core head 7 and the rearward end of the indicator device 15. In the disposition shown in FIG. 9, the compression spring 16 is essentially relaxed. On account of the tensioning forces arising, the compression spring 16 is to be larger in diameter and stiffer than the windings 11.

Figure 10:
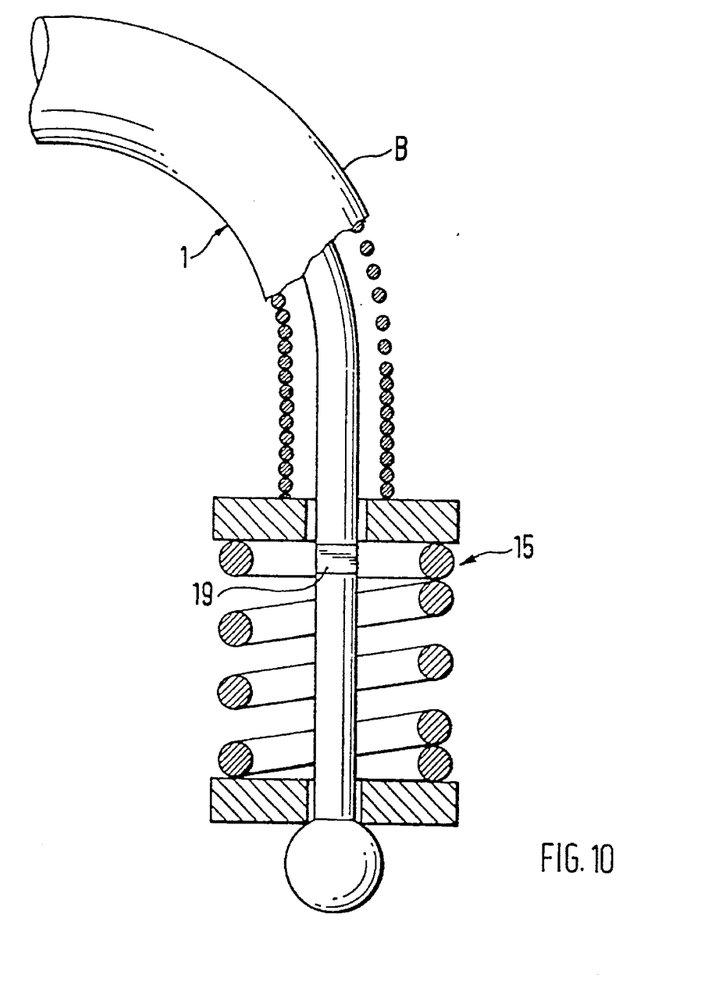
FIG. 10 shows the probe according to FIG. 9 in its stiffened disposition.

When probe 1 is bent by the user in the rearward region projecting out of the body cavity, in accordance with FIG. 10, the relative displacement between sheath 2 and core 3 occurs—as in the above-described embodiments—, whereby the rearward core head 7 is drawn in, presses against the compression spring and compresses this. Hereby the tensioning force causing the stiffening is determined by the force of pressure of tension spring 16. The distance covered by the core 3b is of a size which depends upon the tensioning force. This distance is thus an indicator for the tensioning force. For this reason the distance and/or the tensioning force can be recognized by means of marking on the core 3 and the sheath 2. With the present configuration, marking 19 is formed on core 3b by a line or the edge of a field 19a which is preferably red-colored. The safety limit may be reached e.g. when marking 19 coincides with the rearward end of the sheath 2.

With this configuration the initial compression force of the compression spring 16 is to be sufficiently large as to be adequate as tensioning force for the stiffening of the probe 1.

Figure 11:
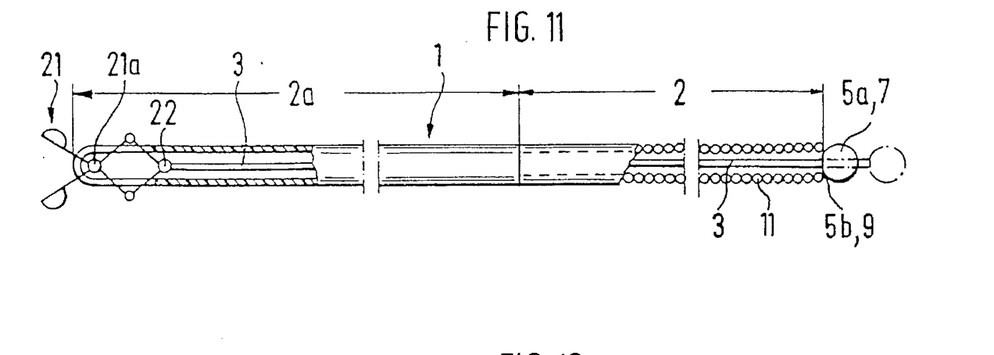
FIG. 11 shows a probe according to the invention with biopsy forceps at the forward end thereof and with opened biopsy forceps.
Figure 12:
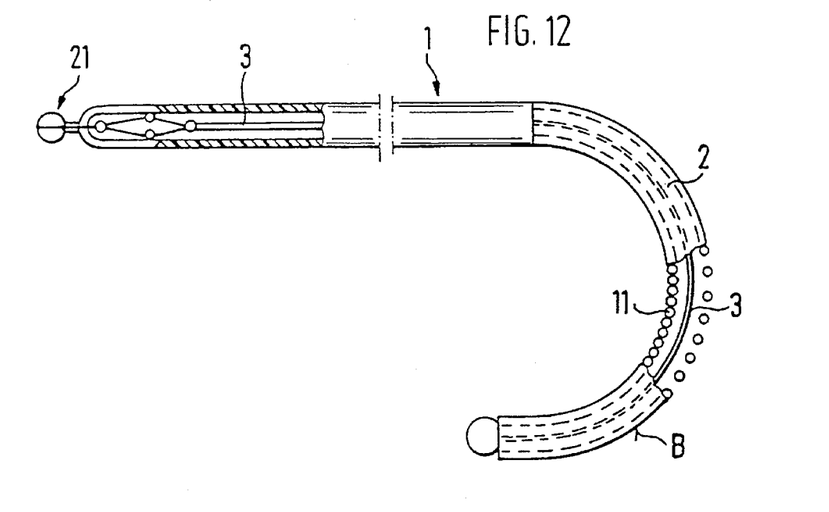
FIG. 12 shows a probe according to FIG. 11 with closed biopsy forceps.

With the configurations according to FIGS. 11 and 12, the probe 1 has associated therewith, at its forward end, a pair of biopsy forceps 21—known per se—in a forceps joint 21a arranged on the sheath, the forceps parts and scissors drive of which are known per se, so that description of further details can be dispensed with. The core 3 is connected with the rearward scissors joint 22. As a stiffening of probe 1 is not required in this configuration, only the rearward section of the sheath, designated as 2, is formed with elements arranged longitudinally one after the other, in particularly windings 11. The remaining section 2a can be formed with a flexible pipe or tube made of metal or plastics, which should be as little compressible as possible in the longitudinal direction. If sheath 2 in this configuration has windings 11 having a spacing a from one another (FIG. 1), the core head 7 on the rearward end of the core 3 can be arranged on the rearward end of the sheath 2. If the elements or windings 11 of the sheath 2 lie against each other the displacement tolerance S is to be provided between the core head 7 and the sheath 2. With biopsy forceps 17, an additional displacement tolerance can be provided if appropriate, in order to realize the opening of the biopsy forceps 21 by manual advancing of the core 3 before taking a specimen. With this configuration, the relative displacement occurring between sheath 2 and core 3—namely their insertion—upon bending of probe 1 in the rearward section thereof, projecting from the body cavity, is utilized to close the biopsy forceps 21. This movement of core 3 is readily achieved by bending the probe 1 once or several times. With this configuration, the solution according to this invention proves to be a driving device, which is integrated into probe 1.

Figure 13:
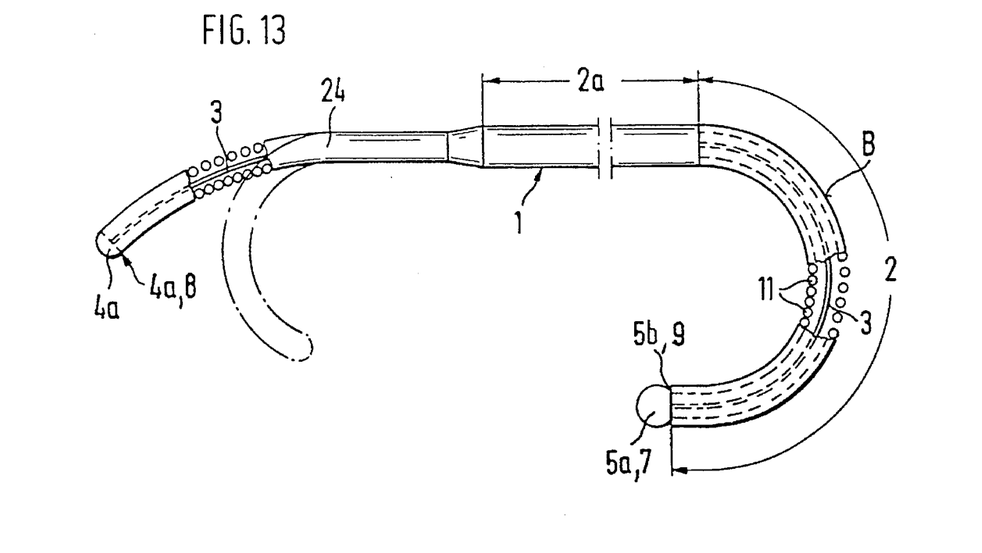
FIG. 13 shows a probe according to the invention with a laterally deflectable tip as so-called guiding probe, in two functional dispositions.

The guiding probe according to FIG. 13 functions in a way comparable to that described above. With this configuration, the core 3 is attached—in a manner known per se—to the forward end of a guiding sheath 24, which if appropriate may be tapered in section, which can consist of material which is elastically bendable, such as plastic or can consist of metal in the form of windings. The remaining part of the sheath 2a, projecting rearwardly from the guiding sheath 24, also consists of a flexible pipe or tube, and has in its rearward region a sheath 2 consisting of elements arranged one after the other or consisting of windings. The above-described features relating to the rear section of the probe 1 according to FIGS. 11 and 12 also apply to the guiding probe 1 according to FIG. 13, so that these features of configuration need not be repeated. Dependant upon purposive bending of the probe 1 in the rearward region thereof according to FIG. 13, a purposive lateral deflection of the guiding sheath 24 can be caused. Upon return bending of the probe 1, the guiding mantle 24 automatically springs back into its initial disposition, which is usually slightly curved. With this configuration, the solution according to the invention presents itself as an integrated driving device.

Figure 14:
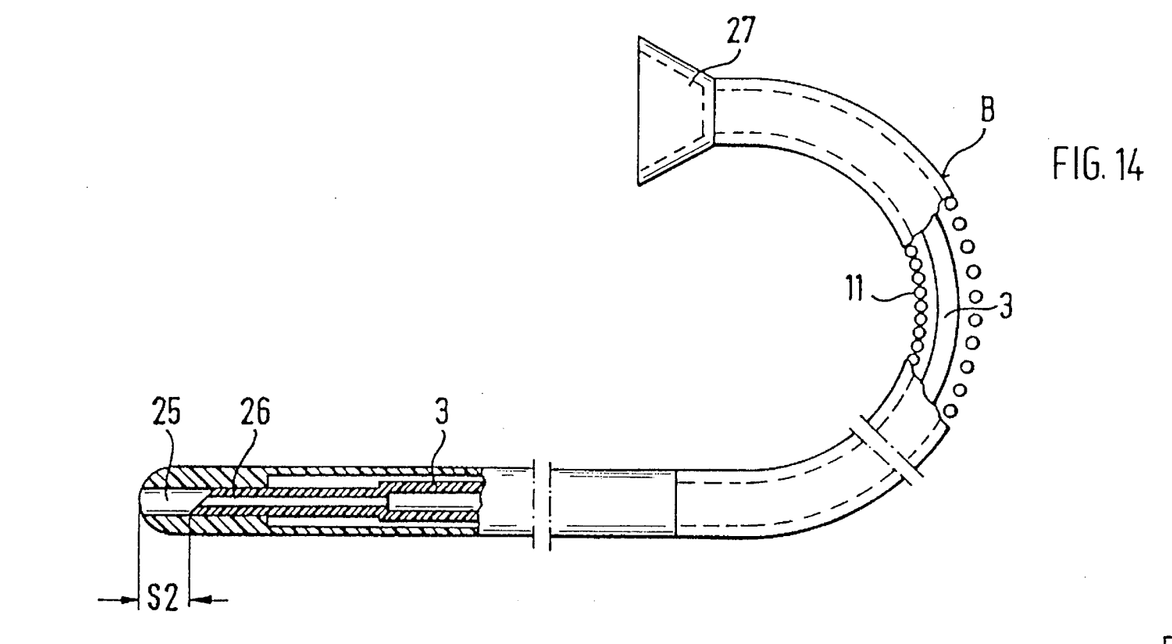
FIG. 14 shows a probe according to the invention with a sclerosation cannula at its forward end, in the insertion position of the probe.
Figure 15:
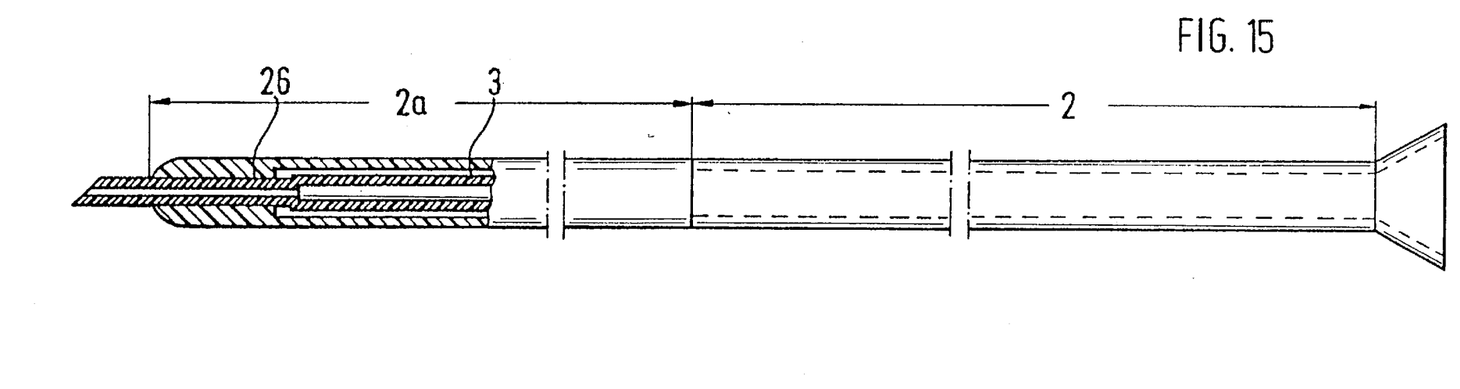
FIG. 15 shows the probe according to FIG. 14 in its injection disposition.

The latter also applies to the embodiment according to FIGS. 14 and 15. However, with this solution, by bending of the probe 1 from the curved position thereof according to FIG. 14 into the straight position thereof according to FIG. 15, instead of a pulling or tensioning movement, a pushing or thrusting movement of the core 3 is generated. With this configuration also, only in its rearward region is the sheath 2 formed with elements arranged one after the other, in particular windings 11 as described above. The remaining sheath region 2a is an elastically flexible pipe or tube made of metal or plastics. Also in this sheath there is a coaxial guiding conduit, preferably being of the same cross-sectional size in the sheath region 2 and the sheath region 2a, and which can run out with the same cross-sectional size at the forward end of the sheath 2a. In this round guiding conduit a core 3 is accommodated longitudinally displaceably, with a small radial clearance for movement, formed by a flexible pipe or a cannula. At the forward end thereof, the core 3 can be connected with a hollow needle 26, which is mounted in the forward end region of the sleeve 2a, longitudinally displaceable in a guide hole 25, preferably of a smaller diameter than the longitudinal conduit. In the rearward region, the core 3 is fixedly connected with a syringe connector, in particular a syringe cone 27, which lies against the rear end of sheath 2a and is attached there. In this way the rearward end of the core 3 is fixedly connected with the rearward end of the sheath 2, not being displaceable relative thereto. The length of the core 3 and of the hollow needle 26 is such that in the straight, extended disposition of the probe 1, the hollow needle 26 projects beyond the forward end of the sheath 2a by the extent of an injection penetration depth. By bending the rearward end region of the probe in the region of the sheath 2 correspondingly with the above described embodiments, the hollow needle 26 is retracted, as is shown in FIG. 14, on account of the relative displacement occurring between the sheath 2, 2a and the core 3. A further retraction of the hollow needle 26, with a greater bending B, is not harmful. With this configuration, the probe 1 is inserted into a body cavity in bent condition (bend B) of its sheath region 2, into which the hollow needle 26 is retracted. It is advantageous to leave in this condition an inwardly directed spacing between the tip of the hollow needle 26 and the forward end of the sheath 2a, so that there is available a displacement tolerance—here designated with S2—corresponding to displacement tolerance of the embodiments of FIGS. 1 and 2, and the probe 1 is able to adapt to curved body cavities, without the needle 26 leaving the sheath 2a. The injection occurs in the target position of probe 1 in the body cavity in the extended condition of the probe according to 15. For this purpose, a syringe is applied at the connecting cone 27 and is injected through the hollow core 3. It is advantageous to withdraw probe 1 from the body cavity in a bent condition according to FIG. 14.

In the embodiment according to FIGS. 14 and 15 the invention comprehends, in contrast to the embodiments according to FIGS. 11 to 13, a thrust or pushing driving device which is integrated into the probe, rather than a tensioning or pulling driving device.

In all the embodiments it is advantageous to fabricate the core 3 of a plastics material which is tension or compression proof. For this purpose Aramid or Keflar® is very suitable.

It is also advantageous to form the core to be elastic in tension, e.g. of a material elastic in tension, such as plastics. Such a configuration is particularly advantageous for stiffening probes 1 in order to hinder breaking of the core 3 or tearing off of movement limiting parts attached thereupon. The elasticity should be so great that the tensioning force exerted by the core is sufficient for stiffening the probe 1.

The configuration according to FIGS. 6 to 8 is suitable, with regard to the arrangement and formation of the spacers, also for the embodiments according to FIGS. 10 to 13.

A bending of the probe 1 in particular in the rearward end region thereof for the purpose of stiffening the probe or the execution of particular functions, for example according to the embodiments of FIGS. 11 to 13, involves manual operational effort. Even the maintaining of the probe in the bent disposition involves an operational effort and also requires the attention of the user of the probe 1. Also, for bending as well as for maintaining the bending, one hand of the user is required, so that for other activities only one hand of the user remains free. It is therefore advantageous to provide for the probe 1 a device for bending and/or for maintaining the bending. In particular during maintenance of the bending by means of a suitable device, the user has both hands free for further activities, provided that the device maintaining the probe 1 in a bent disposition can be deposited on a carrier or can be placed in a holder.

Figure 16:
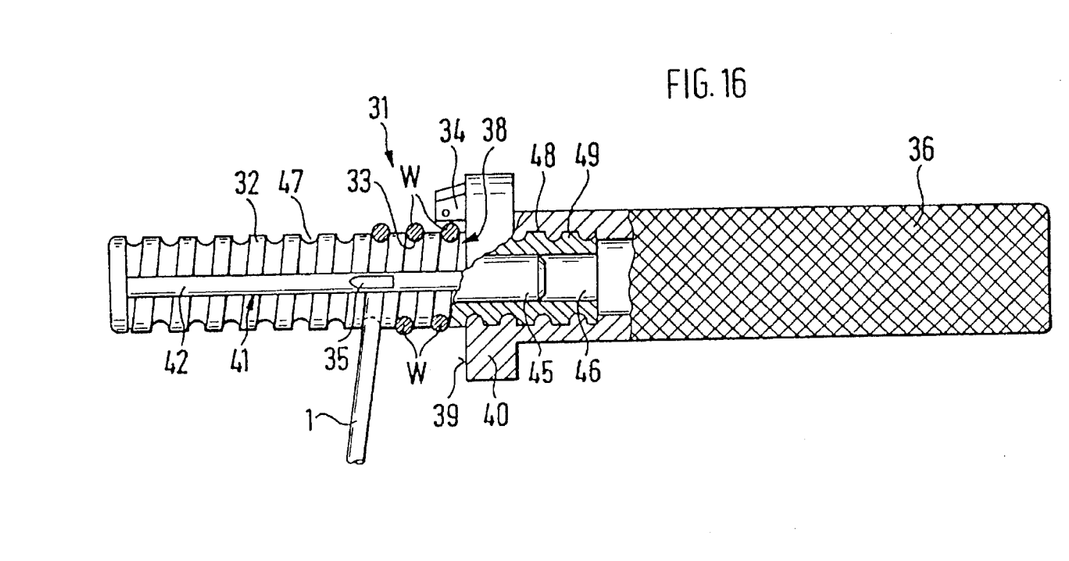
FIG. 16 shows a device for the winding up and retaining the rearward end regions of the probe, in side view partly sectioned longitudinally.
Figure 17:
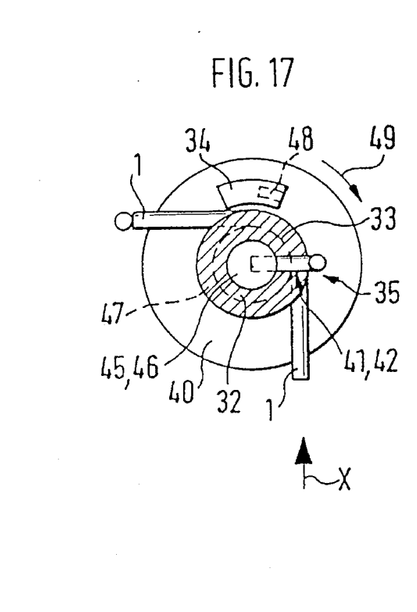
FIG. 17 shows the device according to FIG. 16 in front view.
Figure 18:
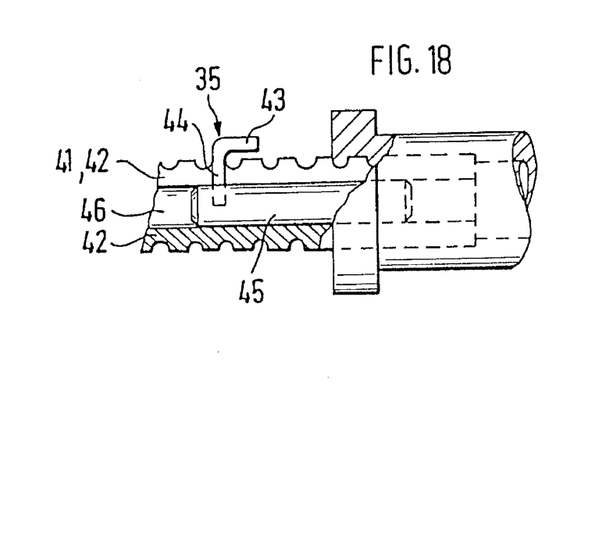
FIG. 18 shows the device in the direction of view of arrow X in FIG. 17.

Such a device for the bending of the probe and the maintenance of the bending is illustrated in FIGS. 16 to 18 and is designated as 31. The device 31 has a bending pin 32 with a rounded bending surface 33, around which probe 1 can be bent. The bending pin 32 is preferably so long that the probe 1 can be wound round it in several turns or windings W lying next to one another. The device 31 has two retaining elements 34, 35 which ensure the retention of the probe 1 in the region of bending thereof. The retaining elements 34, 35 are spaced apart in the direction of winding, or circumferential direction, of the bending pin 32, the bending surface 33 lying therebetween.

The device 31 fulfils its purpose, if it retains the bent probe in its bent disposition. This can be achieved by engagement over of the bent section of probe 1. According to the present configuration, two over-engaging elements are provided, arranged on the bent section of the probe 1, spaced from one another in the direction of winding, against which the bent section of probe 1 lies on account of its bending tension and is thereby retained. It is also advantageous to provide the device 31 with a gripping arrangement, with which the device can be held.

In the present configuration the device 31 has an elongate, straight bending pin 32, which advantageously extends coaxially or in alignment from a bar-like handle 36, having in particular a round section. Both the retaining elements 34, 35, are retention brackets in the form of axial protrusions, arranged at such a radial spacing from bending pin 32 that the bent section of probe 1 finds space between. The second retaining element 35 is preferably displaceable in the longitudinal direction of the winding pin 32, so that the probe 1 can be bent also in several windings W, lying side by side in the longitudinal of the winding pin 32, and this retaining element 35 can be adjusted to the resulting axial length of the winding.

In the present configuration, the first retaining element 34 is arranged on a forwardly directed shoulder surface 39 of the handle 36, which here may have a collar 40. The second retaining element 35 is, in relation to the first retaining element 34, offset in the circumferential or winding direction and is selectively displaceable in an axial guide 41 which formed by a longitudinal groove 42 in the winding pin 32, essentially extending from the shoulder surface 39 to the free end part of winding pin 32. The second retaining element 35 formed with an angle shape, with an axial bracket arm 43 and an radial bracket arm 44 carrying the axial arm. The radial bracket arm 44 is fastened to a pin-shaped sliding piece 45, in particular fixedly set in a radial bore. This sliding piece 45 is displaceably mounted in a coaxial longitudinal bore 46 in the winding pin 32, with clearance for movement, whereby the longitudinal groove 42 extends into the longitudinal bore 46 in the form of a slit and the radial bracket arm 44 penetrates the longitudinal groove 42. The axial bracket arm 43 is preferably directed rearwardly, that is, in the direction of the first retaining element 34.

In the present configuration a receiving groove 47 for the probe 1 is worked in the outer surface of the winding pin, in the manner of a helix, and can extend to the forward end of the winding pin. Hereby an orderly winding is possible, and little attention is needed for this procedure. As the wound section of the probe 1 is arranged sunk into the receiving groove 47 in the winding pin 32, the retaining elements 34, 35 need only engage over the associated winding, that is, a radial spacing from the outer surface of the winding pin 32 may be smaller or non-existent, if the sectional dimensioning of the receiving groove 47 corresponds with the diameter of the probe 1.

In the present configuration, the device 31 with the winding pin 32 and the handle 36 is provided in two parts, whereby the winding pin 32 is with its rearward end fixedly set or screwed into a receiving hole 48 of the preferably sleeve-form handle 36 by means of an engagement of the lands 49, present between the helix-like receiving groove 47, into a corresponding internal thread in the forward end part of the handle 36.

For a winding process the rear end of the probe 1 is inserted into the receiving groove 47 running under the first retaining element 34 and forming the draw opening 38, and then the probe 1 is wound onto the winding pin 32 and into the helix-form receiving groove 42, with selected windings W, until the probe is stiffened or has carried out the intended function. In as far as this functional disposition is to be maintained, the second retaining element 35 is displaced axially towards the windings W, until it engages over the forwardmost winding W. Through the bending tension present, the retaining element 35 is held in the over-engaging position thereof. In this disposition both operational hands of the user are free to be used for other purposes.

In the protrusion forming the first retaining element 34 a blind hole 48 is arranged, which is open in the direction of the bending or winding (arrow 49).

The device 31 or the winding pin 32 and the handle 36 preferably consist, along with all other individual parts, in particular of aluminium.

I claim:

1. A probe (1) for the implementing of medical procedures in cavities of the body, consisting of an elastically flexible sheath (2), which is formed by a plurality of relatively movable sheath elements (11) arranged in sequence along the longitudinal direction of said sheath, and a core (3), first positional setting means (5a, 5b) being located between the sheath (2) and the core (3) in a rearward proximal region of the probe, and second positional setting means (4a, 4b) being arranged between the sheath (2) and the core (3) in a forward distal region of the probe and which facilitate the presence of a displacement tolerance (S) between sheath (2) and core (3), whereby by bending (B) of the probe (1) in the rearward proximal region thereof which projects out of the body cavity, there is effected a relative displacement between the sheath (2) and the core (3) or a pushing or pulling force between the sheath (2) and the core (3) so as to stiffen the probe (1) in said forward distal region in that the sheath elements (11) are caused to lie against one another along the inner side of the bend (B) causing the displacement tolerance (S) to be taken up, and along the outside of the bend the sheath elements are spaced further apart from one another such that the strength or rigidity of the stiffening effect is selectively determined by the degree of the bending and the length of the bend (B).

2. The probe according to claim 1, wherein one of the positional setting means is formed by a fastening and the other positional setting means is formed by a pair (5a, 5b, 4a, 4b) of longitudinal displacement limiting elements wherein said pair of other positional setting means determines the displacement tolerance (S).

3. The probe according to claim 1, wherein the sheath (2) in at least in a rearward region or over the entire length thereof is wound from a band or wire into windings in the form of a helix, the windings (11) lying one against the other or at least a part of the windings being at a spacing (a) from one another.

4. The probe according to claim 2, wherein the pair of longitudinal displacement limiting elements (5a, 5b, 4a, 4b) is respectively each formed by a core head (6, 7) which cooperates with a facing shoulder (8, 9, 13) on the sheath (2).

5. The probe according to claim 4, wherein the core heads (6, 7) cooperate with the ends (8, 9) of the sheath (2).

6. The probe according to claim 1, wherein opposite ends of said probe are similarly configured.

7. The probe according to claim 1, wherein there is selectively associated therewith in the rearward region, a travel and force detector, such as a pulling force detector (15), indicating the relative displacement.

8. The probe according to claim 7, wherein the selective travel and force detector (15) has a spring, in the form of a compression coil spring (16) which is located in the rearward end region of the probe (1) between the sheath (2) and the displacement limiting element part (7) of the core (3).

9. The probe according to claim 7, wherein markings (19) correlated with one another are provided on the sheath (2), or on the selective travel and force detector (15) attached to the sheath, and on the core (3), or on elements attached to the core.

10. The probe according to claim 7, wherein the spacing between the displacement limiting element parts (6, 7) arranged on the core (3), if applicable including the selective travel and force detector (15), is greater than the spacing between the displacement limiting element parts (4b, 5b) associated with the sheath (2) and with the addition of the displacement tolerance (S) and a spacer (14) is associated with the probe (1), whereby spacer can be selectively set between the rearward displacement limiting element part (7) associated with the core (3) and the rearward displacement limiting element part (5b) associated with the sheath (2) or the selective travel and force detector (15).

11. The probe according to claim 10, wherein the length (L) of the spacer (14) corresponds to the difference between the displacement limiting element parts (6, 7) associated with the core (3) and the displacement limiting element parts (4b, 5b) associated with the sheath (2), or is less than this difference by approximately the displacement tolerance (S1).

12. The probe according to claim 10, wherein the spacer (14) is formed by a U-profile piece.

* * * * *